United States Patent
Smith et al.

(10) Patent No.: US 7,718,122 B2
(45) Date of Patent: May 18, 2010

(54) CARRIERS FOR HYPOCHLOROUS ACID VAPOR

(75) Inventors: William L. Smith, Pleasanton, CA (US); Lachelle Arnt, Pleasanton, CA (US); Diane Mellett, San Francisco, CA (US)

(73) Assignee: The Clorox Company, Oakland, CA (US)

( * ) Notice: Subject to any disclaimer, the term of this patent is extended or adjusted under 35 U.S.C. 154(b) by 542 days.

(21) Appl. No.: 11/741,401

(22) Filed: Apr. 27, 2007

(65) Prior Publication Data

US 2007/0217946 A1    Sep. 20, 2007

Related U.S. Application Data

(63) Continuation-in-part of application No. 11/111,012, filed on Apr. 21, 2005, which is a continuation-in-part of application No. 10/828,571, filed on Apr. 20, 2004, now abandoned.

(51) Int. Cl.
- A61L 9/00 (2006.01)
- A62B 7/08 (2006.01)
- A01M 13/00 (2006.01)
- A61K 7/20 (2006.01)
- A61K 7/36 (2006.01)
- A61K 7/50 (2006.01)
- A61B 17/06 (2006.01)
- B65D 25/08 (2006.01)
- A62D 3/00 (2007.01)

(52) U.S. Cl. .......... 422/37; 422/1; 422/5; 422/124; 43/124; 43/125; 424/53; 424/67; 424/76.1; 206/63.3; 206/219; 510/143; 252/187.23; 252/186.36

(58) Field of Classification Search ........ 422/1, 422/5, 37, 124; 43/124, 125; 424/53, 67; 424/76.1; 206/63.3, 219; 510/143; 252/187.23; 252/186.36

See application file for complete search history.

(56) References Cited

U.S. PATENT DOCUMENTS

| | | |
|---|---|---|
| 3,393,155 A | 7/1968 | Schutte et al. |
| 3,622,276 A | 11/1971 | Haahti et al. |
| 3,730,789 A | 5/1973 | Mueller et al. |
| 4,008,170 A | 2/1977 | Allan |
| 4,752,422 A | 6/1988 | Uchida |
| 5,342,597 A | 8/1994 | Tunison, III |
| 5,820,822 A * | 10/1998 | Kross .......................... 422/37 |
| 6,455,751 B1 | 9/2002 | Hoffman et al. |
| 6,528,014 B1 * | 3/2003 | Parkhurst et al. .............. 422/5 |
| 6,569,353 B1 | 5/2003 | Giletto et al. |
| 6,602,466 B2 | 8/2003 | Hamilton et al. |
| 6,605,308 B2 | 8/2003 | Shane et al. |
| 6,607,696 B1 * | 8/2003 | Hamilton et al. .............. 422/37 |
| 6,673,137 B1 | 1/2004 | Wen |
| 6,716,885 B1 | 4/2004 | Twydell et al. |
| 6,936,220 B2 | 8/2005 | Hoshino et al. |
| 2002/0038768 A1 | 4/2002 | Kasuya |
| 2002/0176885 A1 | 11/2002 | Najafi et al. |
| 2002/0179884 A1 | 12/2002 | Hoshino et al. |
| 2003/0138498 A1 | 7/2003 | Yoshikawa et al. |
| 2003/0156980 A1 | 8/2003 | Fischer et al. |
| 2003/0160209 A1 | 8/2003 | Hoffman et al. |
| 2003/0180385 A1 | 9/2003 | Martinelli et al. |
| 2004/0001777 A1 | 1/2004 | Hobson et al. |
| 2004/0146620 A1 | 7/2004 | Iwashita et al. |
| 2005/0214386 A1 | 9/2005 | Shaheen et al. |
| 2005/0216291 A1 | 9/2005 | Shaheen et al. |
| 2005/0221113 A1 | 10/2005 | Bitowft et al. |
| 2005/0232847 A1 | 10/2005 | Bromberg et al. |
| 2005/0232848 A1 | 10/2005 | Nguyen et al. |
| 2005/0233900 A1 | 10/2005 | Smith et al. |
| 2005/0235830 A1 | 10/2005 | Hughes |
| 2005/0265904 A1 | 12/2005 | Hardy et al. |
| 2005/0271559 A1 | 12/2005 | Ratcliff |
| 2007/0217946 A1 | 9/2007 | Smith |
| 2008/0003171 A1 | 1/2008 | Smith |
| 2009/0175958 A1 | 7/2009 | Shaheen |

FOREIGN PATENT DOCUMENTS

| | | |
|---|---|---|
| JP | 2003-169842 | 3/1999 |
| JP | 2000-197669 | 7/2000 |

* cited by examiner

*Primary Examiner*—Jill Warden
*Assistant Examiner*—Monzer R. Chorbaji
(74) *Attorney, Agent, or Firm*—Alok Goel

(57) ABSTRACT

This invention relates to particulate forms of carrier materials containing an oxidant, especially hypohalite or hypohalous acid, especially a dry particulate form of dilute or concentrated hypochlorite and hypochlorous acid compositions. The invention also relates to uses for these particles, such as for generating hypochlorous acid vapor to control the growth of mold or bacteria, to deactivate allergens and allergen causing agents, and to control odors.

16 Claims, No Drawings

CARRIERS FOR HYPOCHLOROUS ACID VAPOR

CROSS REFERENCE TO RELATED APPLICATIONS

The present application is a continuation-in-part of Copending application Ser. No. 11/111,012, filed Apr. 21, 2005, which is a continuation-in-part of application Ser. No. 10/828,571, filed Apr. 20, 2004 now abandoned, which are incorporated by reference.

BACKGROUND OF THE INVENTION

1. Field of the Invention

This invention relates to dry forms of oxidant compositions, especially a dry form of dilute hypochlorite and hypochlorous acid compositions. The invention also relates to uses for these dry forms of oxidants, including generating hypochlorous acid vapor.

2. Description of the Related Art

U.S. Pat. No. 6,716,885 to Twydell et al., U.S. Pat. No. 5,342,597 to Tunison, III, U.S. Pat. No. 3,393,155 to Schutte et al. and U.S. Pat. No. 4,008,170 to Allan describe water dispersed in hydrophobic silica particles to give what is sometimes referred to as "dry water". U.S. Pat. App. 2003/0160209 to Hoffman et al. describes the preparation of "dry oxone" from 1 N oxone solution and treated fumed silica. U.S. Pat. No. 6,569,353 to Giletto et al. describes a dual system of persulfate and oxidant in a sorbent material and an activator in a sorbent material, where the two gels are mixed together to give a material for decontaminating toxic agents. The sorbent material is selected from silicon dioxide, silica gel, silicon oxyhydroxides, aluminum oxide, alumina gel, aluminum oxyhydroxides, aluminates, other metal oxides, other metal oxyhydroxides, clay minerals and mixtures thereof, preferably, fumed silica. U.S. Pat. No. 3,730,789 to Mueller et al. describes rocket propellant formed by gelling aqueous oxidants with silica gel.

U.S. Pat. App. 2003/0156980 to Fischer et al. produced thickened solutions of 2.7-3% hypochlorite using fumed silica and optional thickeners. U.S. Pat. Appl. 2002/0179884 to Hoshino et al. found that dilute hypochlorite solutions create difficulties in obtaining a formulation with satisfactory storage stability.

SUMMARY OF THE INVENTION

In accordance with the above objects and those that will be mentioned and will become apparent below, one aspect of the present invention is a method of controlling the growth of mold or bacteria comprising the steps of placing at least one particle in a confined space; allowing hypochlorous vapor from the particle to contact the mold or bacteria; inhibiting the growth of mold or bacteria; wherein the particle comprises a carrier and an oxidant.

In accordance with the above objects and those that will be mentioned and will become apparent below, another aspect of the present invention comprises a method of deactivating allergens comprising the steps of placing at least one particle in a confined space; allowing hypochlorous acid vapor from the particle to contact an allergen or allergen generating species; deactivating the allergen or allergen generating species; wherein the particle comprises a carrier and an oxidant.

In accordance with the above objects and those that will be mentioned and will become apparent below, another aspect of the present invention comprises a method of controlling odors comprising the steps of placing at least one particle in a confined space; allowing hypochlorous acid vapor from the particle to contact an odor-causing substance; modifying the odor-causing substance; wherein the particle comprises a carrier and an oxidant.

Further features and advantages of the present invention will become apparent to those of ordinary skill in the art in view of the detailed description of preferred embodiments below.

DETAILED DESCRIPTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the composition alone, not accounting for the substrate weight. Each of the noted composition components and substrates is discussed in detail below.

As used herein, "wiping" refers to any shearing action that the substrate undergoes while in contact with a target surface. This includes hand or body motion, substrate-implement motion over a surface, or any perturbation of the substrate via energy sources such as ultrasound, mechanical vibration, electromagnetism, and so forth.

The term "cleaning composition", as used herein, is meant to mean and include a cleaning formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic and/or amphoteric agents.

The term "confined", as used herein, is meant any limited space; this term includes, for example, rooms, showers, ventilation systems, refrigerators, toy boxes, treatment containers, or other enclosed or partially enclosed areas.

The term "pouch", as used herein, refers to a hollow receptacle defining a volume. The pouch is "closed" in the sense that the actives are substantially retained within the pouch and the pouch volume is substantially sealed around its perimeter. However, the material or materials used to construct the pouch are chosen to allow exit of the gas generated. A pouch can be a sachet, an envelope or a receptacle defining an enclosed surface. The pouch can wholly be constructed from gas permeable layers, or the gas permeable layer can comprise only a portion, e.g. one side of a pouch. The remainder of the pouch can include impermeable materials or other materials.

"Permeable layer," as used herein, refers to a layer that permits passage of gas or vapor generated by an apparatus or other source of the present invention. Permeable layers typically are constructed from polymeric materials. "Impermeable layer," as used herein, refers to a layer that substantially prevents or hinders passage of a generated gas. Impermeable layers can be constructed from various materials, including polymeric material, glass, metal, metallized polymeric material and/or coated papers. As used herein, barrier layers are impermeable layers. The skilled artisan will appreciate that what is considered to be an "impermeable layer" and what is considered to be a "permeable layer" is defined relative to the transmission rates of the respective layers used to construct apparatus of the present invention and the desired gas emission characteristics or shelf life of the product. Relying upon the teachings disclosed herein, and the general knowledge in the art, the practitioner of ordinary skill will require only routine experimentation to identify and/or construct one or more impermeable layers and one or more permeable layers adapted for the purpose at hand.

Carriers

The carriers may take any shape or form, including particles, agglomerates, granules, pellets, briquets, continuous sheets, discontinuous sheets, films, coatings, extruded rods, tubes, and the like. Granules, pellets, or briquets comprise suitable carrier shapes and sizes although other shapes find use such as powders and similar particulate configurations.

U.S. Pat. App. 2005/0233900 to Smith et al. discloses dry powder forms of hypochlorite and is hereby incorporated by reference in its entirety. Suitable carriers can comprise silicas and silicates. Precipitated silicas employed in this regard are produced from solutions of water glass into which sulfuric acid is introduced under fixed conditions. They are formed in the aqueous phase, and depending on the conditions of precipitation, it is possible to produce products with smaller or somewhat larger primary particles, which then basically determine particle size and specific surface area. The precipitates obtained are then washed and dried by methods known in the art. Silicates are also manufactured by a precipitation method, however, the acids which are necessary for precipitation may be replaced partially or completely by solutions of metallic salts such as aluminum sulfate, and the like. The precipitation parameters can also be adjusted to suit the various raw materials.

The silicas and silicates obtained in this way can be dried by a spray drying technique to obtain particles that are substantially spherical, have a size anywhere from about 50 to about 150 µm. Spray dried precipitated silicas may also be ground so that the densities will vary anywhere from about 80 g/l to about 270 g/l, and the particle size anywhere from about 4 µm to 100 µm. Precipitated silicas and silicates can also be dried by standard drying processes, for example in turbodriers or rotating driers. Silicas and silicates dried in this conventional way must always be subsequently ground. The tapped density in this regard can be from about 80 g/l to about 240 g/l, and the particle size from about 4 µm to about 15 µm.

Silicas can also be produced by means of a high temperature flame hydrolysis during which silicon tetrachloride is hydrolyzed in an oxyhydrogen flame, which is sometimes referred to as pyrogenic silica. The tapped density of these silicas is somewhere around 50 g/l. Both the precipitated silicas and the pyrogenic silicas can be post-treated in a secondary stage in order to change the naturally hydrophilic surface to a hydrophobic surface, e.g. by a suitable chlorosilane to react with a silanol group on the surface of the silica.

Suitable silicas include hydrophilic silicas having a surface area of from about 50 to 450 $m^2/g$, an average agglomerate size of from about 3.5 to about 100 µm, or an average primary particle size of from about 12 to 30 nm, a tapped density of from about 50 to 240 g/l, a pH of from about 3.6 to about 9, and a DBP adsorption of about 160 to 335 g/100 g. Suitable silicates may comprise those that have a surface area from about 30 to about 40 $m^2/g$, an average agglomerate size of from about 4 to about 6 µm, a tapped density of from about 285 to 315 g/l, a pH of from about 9.5 to about 10.5, and a DBP adsorption of from about 150 to about 170 g/100 g. The other inorganic carriers will also have substantially the same surface area and particle size, although the density will vary depending upon the material employed. Larger surface areas and particle sizes can also be utilized. Extruded films that are water-soluble or water-permeable can also be effective carriers in certain formulations.

Suitable carriers are silicon dioxide, precipitated silica, fumed silica, silicates, bentonite, synthetic hydrated silicon dioxide, diatomaceous earth, clays, attapulgite, hectorite clay, montmorillonite clay, silica gel particles, zeolite (natural or synthetic), kaolinite, smectite, illite, halloysite, vermiculite, sepiolite, beidelite, palygorskite, talc, metal oxides, etc. and mixtures thereof. Synthetic silicon containing particles are suitable, as it enables a good control of the particle size.

Carrier particles can form agglomerates and the average primary particle size is the size of the agglomerated particle. Precipitated silica materials usually appear in the form of agglomerates. The average agglomerate size of the silica range from about 50 to 100 microns. The silica agglomerates may be milled by various known methods to reduce the agglomerate size to the range of 2 to 15 microns. The pH of the silica is normally from about 5.5 to about 7.0.

The hydrophilic silica can also be a fumed silica. Hydrophilic precipitated silica materials useful herein are commercially available from Degussa Corporation under the names SIPERNAT® 22S, 22LS, 50S. Suitably, the silica gel is in the form of particles. The silica gel particles have an average pore diameter, suitably, from about 8 nm to about 10 nm, and a particle diameter of from about 1 mm to about 5 mm.

Hypohalous Acid Vapor

Hypohalous acid vapor can be formed from a variety of oxidants, including compositions containing hypohalite or hypohalous acid, including sodium hypochlorite and hypochlorous acid. Suitable hypohalous acids and salts may be provided by a variety of sources, including compositions that lead to the formation of positive halide ions and/or hypohalite ions; hypohalous acid, hypohalous acid salt, hypohalous acid generating species, hypohalous acid salt generating species; as well as compositions that are organic based sources of halides, such as chloroisocyanurates, haloamines, haloimines, haloimides and haloamides, or mixtures thereof. These compositions may also produce hypohalous acid or hypohalite species in situ. Suitable hypohalous acids and salts for use herein include the alkali metal and alkaline earth metal hypochlorites, hypobromites, hypoiodites, chlorinated trisodium phosphate dodecahydrates, potassium and sodium dichloroisocyanurates, potassium and sodium trichlorocyanurates, N-chloroimides, N-chloroamides, N-chlorosulfamide, N-chloroamines, chlorohydantoins such as dichlorodimethyl hydantoin and chlorobromo dimethylhydantoin, bromo-compounds corresponding to the chloro-compounds above, and compositions which generate the corresponding hypohalous acids, or mixtures thereof.

In one embodiment, said hypohalite composition comprises an alkali metal and/or alkaline earth metal hypochlorite, or mixtures thereof. Compositions may comprise an alkali metal and/or alkaline earth metal hypochlorite selected from the group consisting of sodium hypochlorite, potassium hypochlorite, magnesium hypochlorite, lithium hypochlorite and calcium hypochlorite, and mixtures thereof.

The anodic oxidation of chloride in an electrolysis cell results in the production of a number of oxychlorine ions including hypochlorite, chlorite, chlorate, and perchlorate. Chlorite is readily oxidized to chlorate. Perchlorate may be an undesirable contaminant in the environment due to its low reactivity, high mobility, and inhibition of thyroid function. The production of hypochlorite via chlorination of caustic water is not believed to result in the formation of perchlorate. This route may be advantageous for certain uses where minor amounts of perchlorate would be undesirable.

The compositions of the invention can be diluted prior to use from a concentrated liquid or solid composition. For instance, liquid, especially aqueous, sodium hypochlorite optionally containing surfactants or other additives of 5.25% available chlorine concentration can be diluted to below 500 ppm available chlorine concentration. Tablets or powders having solid hypochlorite or hypochlorite generators can be dissolved in water to deliver compositions below 500 ppm concentration. Examples of compositions that can be diluted are described in U.S. Pat. No. 6,297,209, U.S. Pat. No. 6,100,228, U.S. Pat. No. 5,851,421, U.S. Pat. No. 5,688,756, U.S. Pat. No. 5,376,297, U.S. Pat. No. 5,034,150, U.S. Pat. No. 6,534,465, U.S. Pat. No. 6,503,877, U.S. Pat. No. 6,416,687, U.S. Pat. No. 6,180,583, and U.S. Pat. No. 6,051,676.

The hypohalous acids and salt composition may be an equilibrium mixture of hypochlorous acid and sodium hypochlorite. The oxidant active species is present in an amount from above zero to about 10 weight percent of the composition, or from about 0.001 weight percent (10 ppm) to about 1 weight percent of the composition, or from about 0.005 (50 ppm) to about 0.05 weight percent of the composition, or 0.5 weight percent or greater of the composition, or less than 0.5 weight percent of the composition.

Other oxidants are also possible including peroxygen compounds such as hydrogen peroxide and other oxidants such as chlorine dioxide. In some embodiments the oxidant or oxidants are effective against mold, mildew, odors, allergens, biofilm, etc. in the absence of any other antimicrobial agent or active ingredient, such as metal ions, quaternary ammonium compounds, or volatile alcohols.

Preparation of Compositions

The particles can be dispersed in an organic phase such as a cream or nonaqueous lotion to provide sanitization of hands or removal of odors from feet or underarms. The particles allow the escape of hypochlorous acid vapor, so they may be used as a source of volatile disinfectant which may be used to control odors and the growth of microorganisms, including mold and bacteria, on food in food storage containers, on articles stored in bags, dressers, closets, etc., on dirty laundry stored in hampers, diapers stored in diaper pails, on trash or garbage in waste containers, and on animal litter such as cat litter. In addition to inhibiting the growth of microorganisms, the hypochlorous acid vapors also prevent odors due to the growth of microorganisms as well as modifying odor-causing substances so that they no longer cause undesirable odors. The hypochlorous acid vapor can also deactivate allergens, for example, by deactivating the allergen or allergen generating species. Since hypochlorous acid vapor destroys allergens, the particles may be particularly useful for treating carpets, upholstery and drapery. The particles are small enough to be applied from an aerosol dispenser as well as a shaker can. Combining the ability of allergen destruction and the release of hypochlorous acid may reduce airborne allergens in the vicinity of pet areas such as bird or rodent cages, dog kennels, and cat boxes. The particles also expand the possibility of formulating hypochlorite-containing products with other ingredients. The dry particles can be combined with a variety of other dry ingredients that may or may not be kept separate until used.

The amount of available halogen oxidant in the composition is determined by placing samples of the composition into about 50 milliliters of distilled water, followed by addition of about 10 milliliters of a 10 weight/weight percent solution of potassium iodide and addition of about 10 milliliters of a 10 volume percent solution of sulfuric acid, the resulting mixture being well stirred. A surfactant that does not react rapidly with hypochlorous acid can be added to facilitate the release of hypochlorite from the particles. The resulting yellow to brown solution, whose color is the result of oxidation of free iodine ion ($I^-$) to molecular iodine ($I_2$), is then volumetrically titrated to an essentially colorless endpoint by addition of standardized 0.01 or 0.1 Molar sodium thiosulfate ($Na_2S_2O_3$) titrant. Calculation then expresses the result as percent of available molecular chlorine ($Cl_2$), that is to say assigning two equivalents per mole of titrated hypohalite oxidant. Stability results are then expressed by repeated assays over time using identically prepared samples originating from the same composition, normalized to 100 percent representative of the starting available chlorine measured initially.

Surfactants

The composition of the invention may contain surfactants. The surfactants should be stable to hypohalous acid or hypohalous acid salt unless they are physically isolated. Examples of surfactants having relatively good stability can be found in U.S. Pat. Nos. 6,413,925 and 5,851,421.

The composition may contain one or more surfactants selected from anionic, nonionic, cationic, ampholytic, amphoteric and zwitterionic surfactants and mixtures thereof. A typical listing of anionic, nonionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. Where present, ampholytic, amphoteric and zwitteronic surfactants are generally used in combination with one or more anionic and/or nonionic surfactants. The surfactants may be present at a level of from about 0% to 90%, or from about 0.001% to 50%, or from 0.001% to 1.0%, or from about 0.01% to 25% by weight.

Solvent

The composition of the invention may contain solvents. The solvents should be stable to hypohalous acid or hypohalous acid salt if long term storage is desired. If the solutions of the composition are generated prior to use, then solvents having less stability may be used. The solvents can be present at a level of from 0.001% to 10%, or from 0.01% to 10%, or from 1% to 4% by weight.

Additional Adjuncts

The compositions optionally contain one or more of the following adjuncts: stain and vapor pressure modifiers, soil repellants, lubricants, odor control agents, perfumes, fragrances and fragrance release agents, brighteners, and fluorescent whitening agents. Other adjuncts include, but are not limited to, acids, electrolytes, dyes and/or colorants, solubilizing materials, stabilizers, thickeners, defoamers, hydrotropes, cloud point modifiers, preservatives, and other polymers. The solubilizing materials, when used, include, but are not limited to, hydrotropes (e.g. water soluble salts of low molecular weight organic acids such as the sodium and/or potassium salts of toluene, cumene, and xylene sulfonic acid). The acids, when used, include, but are not limited to, mineral acids, organic hydroxy acids, citric acids, keto acid, and the like. Electrolytes, when used, include, calcium, sodium and potassium chloride. Thickeners, when used, include, but are not limited to, polyacrylic acid, xanthan gum, calcium carbonate, aluminum oxide, alginates, guar gum, methyl, ethyl, clays, and/or propyl hydroxycelluloses. Defoamers, when used, include, but are not limited to, silicones, aminosilicones, silicone blends, and/or silicone/hydrocarbon blends.

Preservatives, when used, include, but are not limited to, mildewstat or bacteriostat, methyl, ethyl and propyl parabens, phosphates such as trisodium phosphate, short chain organic acids (e.g. acetic, lactic and/or glycolic acids), bisguanidine compounds (e.g. Dantagard® and/or Glydant®) and/or short chain alcohols (e.g. ethanol and/or IPA). The mildewstat or bacteriostat includes, but is not limited to, mildewstats (including non-isothiazolone compounds) including Kathon GC, a 5-chloro-2-methyl-4-isothiazolin-3-one, KATHON® ICP, a 2-methyl-4-isothiazolin-3-one, and a blend thereof, and KATHON® 886, a 5-chloro-2-methyl-4-isothiazolin-3-one, isothiazolin-3-one, all available from Rohm and Haas Company; BRONOPOL®, a 2-bromo-2-nitropropane 1,3 diol, from Boots Company Ltd., PROXEL® CRL, a propyl-p-hydroxybenzoate, from ICI PLC; NIPASOL® M, an o-phenyl-phenol, Na$^+$ salt, from Nipa Laboratories Ltd., DOWICIDE® A, a 1,2-Benzoisothiazolin-3-one, from Dow Chemical Co., Nipacides from Clariant, and IRGASAN® DP 200, a 2,4,4'-trichloro-2-hydroxydiphenylether, from Ciba-Geigy A.G.

Antimicrobial Agent

The composition of the invention may contain antimicrobial agents. The antimicrobial agents should be stable to hypohalous acid or hypohalous acid salt if long term storage is desired. If the solutions of the composition are generated prior to use, then antimicrobial agents having less stability may be used.

Antimicrobial agents include quaternary ammonium compounds and phenolics. Non-limiting examples of these quaternary compounds include benzalkonium chlorides and/or substituted benzalkonium chlorides, di($C_6$-$C_{14}$)alkyl di short chain ($C_{1-4}$ alkyl and/or hydroxyalkyl) quaternaryammonium salts, N-(3-chloroallyl)hexaminium chlorides, benzethonium chloride, methylbenzethonium chloride, and cetylpyridinium chloride. Other quaternary compounds include the group consisting of dialkyldimethyl ammonium chlorides, alkyl dimethylbenzylammonium chlorides, dialkylmethylbenzylammonium chlorides, and mixtures thereof. Biguanide antimicrobial actives include, but are not limited to polyhexamethylene biguanide hydrochloride, p-chlorophenyl biguanide; 4-chlorobenzhydryl biguanide, halogenated hexidine such as, but not limited to, chlorhexidine (1,1'-hexamethylene-bis-5-(4-chlorophenyl biguanide) and its salts are also in this class.

Builder/Buffer

The composition of the invention may contain a builder or buffer. The builder or buffer should be stable to hypohalous acid or hypohalous acid salt if long term storage is desired. If the solutions of the composition are generated prior to use, then builders or buffers having less stability may be used.

The composition may include a builder or buffer, which can be used as a pH adjusting agent or as a sequestering agent in the composition. A variety of builders or buffers can be used and they include, but are not limited to, phosphate-silicate compounds, carbon dioxide or carbonate, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxysulfonates, and starch derivatives.

Builders or buffers can also include polyacetates and polycarboxylates. The polyacetate and polycarboxylate compounds include, but are not limited to, sodium, potassium, lithium, ammonium, and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. These builders or buffers can also exist either partially or totally in the hydrogen ion form.

The builder agent can include sodium and/or potassium salts of EDTA and substituted ammonium salts. The substituted ammonium salts include, but are not limited to, ammonium salts of methylamine, dimethylamine, butylamine, butylenediamine, propylamine, triethylamine, trimethylamine, monoethanolamine, diethanolamine, triethanolamine, isopropanolamine, ethylenediamine tetraacetic acid and propanolamine.

Buffering and pH adjusting agents, when used, include, but are not limited to, organic acids, mineral acids, alkali metal and alkaline earth salts of silicate, metasilicate, polysilicate, borate, hydroxide, carbonate, carbamate, phosphate, polyphosphate, pyrophosphates, triphosphates, tetraphosphates, ammonia, hydroxide, monoethanol-amine, monopropanolamine, diethanolamine, dipropanolamine, triethanolamine, and 2-amino-2methylpropanol. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are tri (hydroxymethyl) amino methane (TRIS), 2-amino-2-ethyl-1, 3-propanediol, 2-amino-2-methyl-propanol, 2-amino-2-methyl-1,3-propanol, disodium glutamate, N-methyl-diethanolarnide, 2-dimethylamino-2-methylpropanol (DMAMP), 1,3-bis-(methylamine)-cyclohexane, 1,3-di-amino-propanol N,N'-tetra-methyl-1,3-diamino-2-propanol, N,N-bis(2-hydroxyethyl)glycine(bicine) and N-tris(hydroxymethyl)methyl glycine(tricine). Other suitable buffers include ammonium carbamate, citric acid, acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide.

When employed, the builder, buffer, or pH adjusting agent comprises at least about 0.001% and typically about 0.01-5% by weight of the cleaning composition. Preferably, the builder or buffer content is about 0.01-2%.

Fragrance

The composition of the invention may contain fragrance. The fragrance should be stable to hypohalous acid or hypohalous acid salt if long term storage is desired. If the solutions of the composition are generated prior to use, then fragrances having less stability may be used.

Compositions of the present invention may comprise from about 0.001% to about 5% by weight of the fragrance. Compositions of the present invention may comprise from about 0.005% to about 2.5% by weight of the fragrance. Compositions of the present invention may comprise from about 0.01% to about 1% by weight of the fragrance.

Water and pH

The water should be present at a level of less than about 99.999%. The water may be deionized, filtered to remove impurities including metals and organic carbon, purified by reverse osmosis, purified by distillation, or any combination thereof. Purified water may be prepared by a process selected from the group consisting of sodium cation exchange, hydrogen cation exchange, reverse osmosis, activated carbon treatment, UV light treatment, UVC, ozone treatment, chlorination, ultrafiltration, nanofiltration, electrodialysis, and a combination thereof. During preparation there may be a need for hygiene and segregation to prevent the introduction of compounds that are oxidized by hypochlorite since these become more important at low concentrations where the loss of a few ppm may be significant.

The composition may be adjusted for pH using a pH adjusting agent. Suitable pH adjusting agents include carbon dioxide, alkali metal carbonate, alkali metal bicarbonate, alkali metal silicates, alkali metal hydroxide, alkali phosphate salt, alkaline earth phosphate salt, alkali borate salt, hydrochloric acid, nitric acid, sulfuric acid, alkali metal hydrogen sulfate, acetic acid, vinegar from various sources, other carboxylic acids, polycarboxylates, organic sulfonic acids, sulfamic acid, amine, alkyl amine, dialkyl amine, and trialkyl amine. The composition may have a pH from 1 to 13. The composition may have a pH from 2 to 12. The composition may have a pH from 2 to 5. The composition may have a pH from 5 to 8. The composition may have a pH from 6 to 8. The composition may have a pH from 6 to 7.5. The composition may have a pH from 9 to 11. The composition may have a pH from 9 to 12. The composition may have a pH from 10 to 12.

Application

The composition may be stored, shipped, or applied in a variety of container materials, including glass, ABS, polycarbonate, high density polyethylene, low density polyethylene, high density polypropylene, low density polypropylene, polyethylene terephthalate, or polyvinylchloride In one embodiment of the invention, the method provides a safe and easy way to sanitize hard-to reach and difficult to sanitize objects and locations using dry, airborne technology. The method allows consumers to easily sanitize objects that they know have germs, but are difficult or time-consuming to clean, e.g. children's toys. The composition can be delivered in a variety of forms including a pouch, sachet, a stick-up, a flat disc, and a powder dispenser. The pouch or other form can be vapor permeable, such as Tyvec® (HDPE) pouches. Semipermeable films, membranes or nonwovens that allow hypochlorous acid vapors to largely permeate, but restrict the release of water vapors may also be used (e.g. Goretex® films). The method can be used in a variety of spaces, including toy boxes, closets, laundry hampers, trash cans and diaper pails, behind the toilet, and under the kitchen sink. The method can be used for batch sanitizing, preventing odors, preventing mold and mildew growth, sanitizing objects with "nooks and crannies". Products using this technology both kill germs (Staph) and inhibit mold growth in an enclosed space.

The composition can be used in a method of controlling odors, for example general cooking odors, bathroom or refrigerator odors, or odors from biofilm. The compositions can also control the growth of biofilm. One particular consumer problem is the growth of biofilm in washing machines or dryers, such as the new high efficiency washing machines. These compositions could be used to prevent or control the growth of biofilm in washing machines or control odors from that biofilm. For example a sachet or package containing the composition might be tossed into the washer or attached or otherwise connected to the inside of the washer. Since the composition can be effective by delivering the oxidant vapor, the composition can be effective in a hard to reach area of a laundry appliance.

The composition can be used in a method of controlling the growth of mold or bacteria using the steps of placing at least one particle in a confined space, allowing hypochlorous vapor from the particle to contact the mold or bacteria, wherein the growth of mold or bacteria is controlled or eliminated. The composition can be used in a method deactivating allergens using the steps of placing at least one particle in a confined space, allowing hypochlorous acid vapor from the particle to contact the allergen or allergen generating species, wherein the allergen is deactivated.

During the course of evaluating various oxidants and antimicrobials for their allergen deactivating ability, we have found that a very dilute solution (on the order of 40-80 ppm) of primarily hypochlorous acid can effectively deactivate allergens. Presumably the low levels of oxidant are still able to break up the allergen proteins, rendering them biologically inert. Hypochlorous acid vapor from solutions of higher pH can also be effective.

The compositions of the invention can be used to purify water and make the water safe for consumption or recreational use. The compositions of the invention can be used for algae control. The compositions of the invention can be incorporated into water filters, for example, for use while camping or in disasters.

The compositions of the invention can be used for a direct food treatment, for cleaning food-contact surfaces, and for toxicologically safe cleaning. This may involve the use of additional food-safe ingredients, GRAS ingredients, or ingredients with low toxicologically impact. Methods describing this use and possible compositions can be found in U.S. Pat. No. 6,455,086, U.S. Pat. No. 6,313,049, U.S. Pat. App. 2002/0132742, U.S. Pat. App. 2001/0014655, PCT App. WO99/00025, and U.S. Pat. App. 2002/0151452, which are incorporated by reference herein.

EXAMPLES

Co-pending application Ser. No. 10/828,571, published as U.S. Pat. App. 2005/0232847 filed Apr. 20, 2004 discloses factors in the chemical composition that affect the stability of dilute hypohalous acid and hypohalous acid salt compositions, and is incorporated by reference. The stability of these compositions is also affected by packaging and manufacturing materials. Co-pending application Ser. No. 11/111,012, published as U.S. Pat. App. 2005/0233900 filed Apr. 21, 2005 discloses dry powdered forms of hypochlorite compositions, and is incorporated by reference.

Table I shows silica particles formed by mixing various dilute hypochlorite compositions with hydrophilic silica particles. The hypochlorite compositions (approximately 200 ppm hypochlorite) were stabilized by addition of hydrochloric acid, succinic acid and sodium bicarbonate. The absorbency indicates the weight of aqueous hypochlorite composition that could be absorbed per weight of silica. The silica carrier suitably has an absorbency for 200 ppm hypochlorite solutions of greater than 3, or greater than 5, or about 7 or greater. The stability of the hypochlorite was measured at room temperature (approximately 25° C.) and was captured as percent remaining activity.

TABLE I

| Silica | pH | Additive | Absorbency | Stability |
|---|---|---|---|---|
| CE0506 ®[1] | 7 | Succinic acid | 7 | 37% - 20 days |
| CE0506 ®[1] | 7 | HCl | 7 | 41% - 20 days |
| CE0506 ®[1] | 8.5 | Na Bicarbonate | 7 | 11% - 20 days |
| Grace Grade 3 | 7 | HCl | 1 | Not determined |
| Grace Grade 59 | 7 | HCl | 2.5 | Not determined |
| CG0602 ®[1] | 5.5 | HCl | 8 | 58% - 7 days |
| CG0602 ®[1] | 7 | HCl | 8 | 53% - 7 days |
| CG0602 ®[1] | 5.5 | Succinic acid | 7 | 29% - 22 days |
| Aeroperl ® 300/30[2] | 5.5 | Succinic acid | 3.4 | 21% - 15 days |
| Aerogel ® TLD302[1] | 5.5 | Succinic acid | 9.9 | 24% - 22 days |
| Aerogel ® OGD303[1] | 5.5 | Succinic acid | 9.7 | 34% - 22 days |

[1]Cabot Corp.
[2]Degussa AG.

The type of silica used has a great effect on the amount of bleach absorbed as well as the stability achieved. The CE0506 and the aerogel (OGD303, TLD302) materials had better stability than the other materials tested. These samples were used to test microefficacy of the release of hypoclorous acid vapors. The details of the tests were as follows: 10 uL of bacterial suspension (5% fetal bovine serum, $10^8$ S. aureus CFU/mL) was innoculated onto a 1 inch square glass slide. The slide was then dried at 35° F. for 30 minutes under sterile conditions. After the slides were dry, they were transferred into a 3.07 L Glad® container containing a petri dish (100× 150 mm) with a bleach containing product. The weight, height, and concentration of the bleach containing products were recorded. The containers were closed and allowed to sit at room temperature for 3 hours after which the samples were removed aseptically. The samples were placed in D/E broth and vortexed for 30 minutes. 1 mL of this solution was then transferred into 9 mL of Butterfields buffer and vortexed. The solution was then diluted down as necessary and added to sterile petri dishes containing TSA. The dishes were incubated for 24 to 48 hours and then analyzed for the number of bacterial colonies. The results of the microefficacy testing is as follows: Samples containing silica, either CE0506, Aerogel® OGD303, or med pore Grace grade 59 and neat dilute bleach solution were tested for efficacy. All samples contained 40 g of bleach solution that was 195 ppm at pH 5.5 (adjusted with succinic acid). The control in the test was a Glad® container containing the innoculated glass slides with no bleach product. The glass slides were determined to have an average of $6\times10^6$ CFU/mL before the test and the control slides had an average of $5\times10^6$ CFU/mL after the experiment. All other slides showed complete kill after being exposed to the bleach samples for 3 hours in the closed Glad® containers. These results were further confirmed by looking at the color of the D/E broth which was yellow for the control samples (indicating bacterial growth) and purple for the bleach containing samples (indicating no bacterial growth).

Table II represents calculated chlorine vapor levels for regular and low salt bleach at constant hypochlorous acid vapor concentration from sodium hypochlorite compositions. This table shows that as the pH is raised, it takes a much greater concentration of hypochlorite to give the same hypochlorous acid concentration, but that the ratio of chlorine vapor to hypochlorous acid vapor is also much reduced, especially for low salt hypochlorite. Similar ratios of hypochlorous acid vapor and chlorine vapor are expected from hypochlorite absorbed onto a carrier. Suitable ratios of hypochlorous acid vapor to chlorine vapor may be 250 or greater, or 400 or greater, or 500 or greater, or 550 or greater. Vapor levels of HOCl other about 5 ppm may also be necessary or effective, for example 2 ppm, 10 ppm, 20 ppm, 50 ppm, or 100 ppm. Similar ratios of hypochlorous acid vapor to chlorine vapor may apply.

TABLE II

| NaOCl, mg/L | pH | HOCl vapor ppm | $Cl_2$ vapor ppm | $Cl_2$ vapor ppm Low salt |
|---|---|---|---|---|
| 200 | 5.5 | 5.377 | 0.944 | 0.236 |
| 204 | 6.0 | 5.377 | 0.304 | 0.076 |
| 216 | 6.5 | 5.377 | 0.102 | 0.026 |
| 256 | 7.0 | 5.377 | 0.038 | 0.010 |
| 313 | 7.3 | 5.377 | 0.023 | 0.006 |
| 380 | 7.5 | 5.377 | 0.018 | 0.004 |
| 427 | 7.6 | 5.377 | 0.016 | 0.004 |
| 487 | 7.7 | 5.377 | 0.014 | 0.004 |
| 522 | 7.75 | 5.377 | 0.014 | 0.003 |
| 561 | 7.8 | 5.377 | 0.013 | 0.003 |
| 655 | 7.9 | 5.377 | 0.012 | 0.003 |
| 774 | 8.0 | 5.377 | 0.012 | 0.003 |
| 923 | 8.1 | 5.377 | 0.011 | 0.003 |
| 1110 | 8.2 | 5.377 | 0.010 | 0.003 |
| 1347 | 8.3 | 5.377 | 0.010 | 0.003 |
| 1644 | 8.4 | 5.377 | 0.010 | 0.002 |
| 2018 | 8.5 | 5.377 | 0.010 | 0.002 |
| 2490 | 8.6 | 5.377 | 0.009 | 0.002 |
| 3083 | 8.7 | 5.377 | 0.009 | 0.002 |
| 3830 | 8.8 | 5.377 | 0.009 | 0.002 |
| 4770 | 8.9 | 5.377 | 0.009 | 0.002 |
| 5954 | 9.0 | 5.377 | 0.009 | 0.002 |
| 7445 | 9.1 | 5.377 | 0.009 | 0.002 |
| 9321 | 9.2 | 5.377 | 0.009 | 0.002 |
| 11683 | 9.3 | 5.377 | 0.009 | 0.002 |
| 14657 | 9.4 | 5.377 | 0.009 | 0.002 |
| 18400 | 9.5 | 5.377 | 0.009 | 0.002 |

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself. As such, these changes and modifications are properly, equitably, and intended to be, within the full range of equivalence of the following claims.

We claim:

1. A method of controlling the growth of mold, biofilm, or bacteria comprising the steps of:
   a. placing a composition comprising at least one hypochlorous acid generating particle in a confined space;
   b. allowing hypochlorous acid vapor from the particle to contact the mold or bacteria; and
   c. inhibiting the growth of mold, biofilm, or bacteria;

d. wherein the particle comprises a carrier and an oxidant; and e. wherein the ratio of generated hypochlorous acid vapor to chlorine vapor is 250 or greater.

2. The method of claim 1, wherein the oxidant is selected from the group consisting of hypochlorite, hypochlorous acid, and combinations thereof.

3. The method of claim 1, wherein the carrier is selected from the group consisting of precipitated silica, precipitated silicate, and mixtures thereof.

4. The method of claim 1, wherein the composition is placed in a laundry appliance to control biofilm.

5. The method of claim 1, wherein the carrier has an absorbency of 200 ppm hypochlorite solution of greater than 3.

6. The method of claim 1, wherein the particle is contained within a vapor permeable pouch.

7. A method of deactivating allergens comprising the steps of:

a. placing a composition comprising at least one hypochlorous acid generating particle in a confined space;

b. allowing hypochlorous acid vapor from the particle to contact an allergen or allergen generating species; and c. deactivating the allergen or allergen generating species;

d. wherein the particle comprises a carrier and an oxidant; and e. wherein the ratio of generated hypochlorous acid vapor to chlorine vapor is 250 or greater.

8. The method of claim 7, wherein the oxidant is selected from the group consisting of hypochlorite, hypochlorous acid, and combinations thereof.

9. The method of claim 7, wherein the carrier is selected from the group consisting of precipitated silica, precipitated silicate, and mixtures thereof.

10. The method of claim 7, wherein the carrier has an absorbency of 200 ppm hypochlorite solutions of greater than 3.

11. The method of claim 7, wherein the particle is contained within a vapor permeable pouch.

12. A method of controlling odors comprising the steps of:

a. placing a composition comprising at least one hypochlorous acid generating particle in a confined space;

b. allowing hypochlorous acid vapor from the particle to contact an odor-causing substance; and c. inactivating the odor-causing substance;

d. wherein the particle comprises a carrier and an oxidant; and e. wherein the ratio of generated hypochlorous acid vapor to chlorine vapor is 250 or greater.

13. The method of claim 12, wherein the oxidant is selected from the group consisting of hypochlorite, hypochlorous acid, and combinations thereof.

14. The method of claim 12, wherein the carrier is selected from the group consisting of precipitated silica, precipitated silicate, and mixtures thereof.

15. The method of claim 12, wherein the carrier has an absorbency of 200 ppm hypochlorite solutions of greater than three.

16. The method of claim 12, wherein the particle is contained within a vapor permeable pouch.

\* \* \* \* \*